United States Patent
Bian et al.

(10) Patent No.: US 10,040,740 B2
(45) Date of Patent: Aug. 7, 2018

(54) METHOD FOR THE PREPARATION OF IODOALKANES

(71) Applicants: Hong Kong Baptist University, Hong Kong (HK); Yunnan Minzu University, Kunming (CN)

(72) Inventors: Zhaoxiang Bian, Hong Kong (HK); Baomin Fan, Kunming (CN); Chengyuan Lin, Hong Kong (HK); Yongyun Zhou, Kunming (CN); Jingchao Chen, Kunming (CN)

(73) Assignees: Hong Kong Baptist University, Hong Kong (HK); Yunnan Minzu University, Kunming (CN)

(*) Notice: Subject to any disclaimer, the term of this patent is extended or adjusted under 35 U.S.C. 154(b) by 0 days.

(21) Appl. No.: 15/406,029

(22) Filed: Jan. 13, 2017

(65) Prior Publication Data

US 2017/0204022 A1     Jul. 20, 2017

Related U.S. Application Data

(60) Provisional application No. 62/278,534, filed on Jan. 14, 2016.

(51) Int. Cl.
*C07C 17/02* (2006.01)
*C07C 17/04* (2006.01)
*C07C 17/08* (2006.01)
*C07C 17/087* (2006.01)
*C07C 41/22* (2006.01)

(52) U.S. Cl.
CPC .............. *C07C 41/22* (2013.01); *C07C 17/02* (2013.01); *C07C 17/04* (2013.01); *C07C 17/08* (2013.01); *C07C 17/087* (2013.01)

(58) Field of Classification Search
CPC ......... C07C 17/02; C07C 17/04; C07C 17/08; C07C 17/087
See application file for complete search history.

(56) References Cited

FOREIGN PATENT DOCUMENTS

FR        2858319 A1 * 2/2005 ............. C07B 39/00

OTHER PUBLICATIONS

FR-2858319-A1, Feb. 2005, pp. 1-9; English translation (Year: 2005).*

* cited by examiner

*Primary Examiner* — Medhanit W Bahta
(74) *Attorney, Agent, or Firm* — Spruson & Ferguson (Hong Kong) Limited

(57) ABSTRACT

The present invention relates to an atom economic procedure of preparing iodoalkanes by hydroiodination of alkenes. In particular the present method features the generation of anhydrous hydrogen iodide from atomic hydrogen and iodine in situ by using transition metal precursor and phosphine ligandcatalyst.

14 Claims, No Drawings

METHOD FOR THE PREPARATION OF IODOALKANES

CROSS-REFERENCE TO RELATED APPLICATIONS

This U.S. Non-provisional application claims the benefit of U.S. Provisional Patent Application Ser. No. 62/278,534 filed on Jan. 14, 2016, the disclosure of which is hereby incorporated by reference.

FIELD OF THE INVENTION

The present invention relates to an atom economic procedure of preparing iodoalkanes by hydroiodination of alkenes. In particular, the present method features the generation of anhydrous hydrogen iodide from atomic hydrogen and iodine in situ by using the complex of $Rh(COD)_2BF_4$ and (±)-Binap as a catalyst.

BACKGROUND OF THE INVENTION

Iodoalkanes, also known as alkyl iodides, are ubiquitous precursors and fundamental building blocks in organic synthesis due to their high reaction activities in various reactions such as alkylation, cross-coupling, reduction, addition, esterification, and the organometallic transformations. The common method for the preparation of iodoalkanes relies on the Finkelstein reaction and the iodination of corresponding alcohols. Direct addition of hydrogen iodide to alkenes has provided an atom economic strategy for the facile synthesis of iodoalkanes. Although the addition reaction of hydrogen iodide to alkenes have been introduced in many textbooks, it's reporting is quite limited in literatures due to the low reaction activity of aqueous hydrogen iodide. And the substrate scope also suffers from severe limitations due to the harsh reaction conditions. The reaction of silanes and iodine has provided a method for anhydrous hydrogen iodide generation, and its application in hydroiodination reactions has been reported. However, the unavoidable byproduct, iodo-silane has undermined the utility of this reaction, especially in the chemical industry.

It is an objective of the present invention to provide an atom economic procedure of preparing iodoalkanes by hydroiodination of alkenes.

SUMMARY OF THE INVENTION

The present invention relates to an atom economic procedure of preparing iodoalkanes by hydroiodination of alkenes. In particular the present methodology features the generation of anhydrous hydrogen iodide from atomic hydrogen and iodine in situ by using a transition metal precursor and a phosphine ligand as a catalyst, and the anhydrous hydrogen iodide reacts with alkene to result the corresponding iodoalkane.

In a first aspect of the present invention there is provided a method of producing iodoalkanes comprising hydroiodinating alkene with hydrogen and iodine with a transition metal precursor and a phosphine ligand as catalyst, wherein said metal precursor is selected from the group consisting of rhodium, palladium, iridium, and ruthenium precursor.

In a first embodiment of the first aspect of the present invention there is provided a method of producing iodoalkanes by hydroiodination of alkenes. The method further comprises converting the hydrogen and iodine into anhydrous hydrogen iodide.

In a second embodiment of the first aspect of the present invention there is provided a method of producing iodoalkanes by hydroiodination of alkenes wherein said hydroiodination step is performed in situ and the hydrogen and iodine are atomic hydrogen and iodine.

In a third embodiment of the first aspect of the present invention there is provided a method of producing iodoalkanes by hydroiodination of alkenes wherein the metal precursor comprising $Rh(COD)_2BF_4$, $Rh(CO)_2(C_5H_7O_2)$, $[Rh(COD)Cl]_2$, $Rh(COD)_2SbF_6$, $Rh(COD)_2OTf$, $C_{14}H_{16}Cl_2Rh_2$, $[Ir(COD)Cl]_2$, $Ru(COD)Cl_2$.

In a fourth embodiment of the first aspect of the present invention there is provided a method of producing iodoalkanes by hydroiodination of alkenes wherein the phosphine ligand comprising (±)-Binap, $PPH_3$, DPPE, DPPB, XANTPHOS and tricyclohexyphosphine.

In a fifth embodiment of the first aspect of the present invention there is provided a method of producing iodoalkanes by hydroiodination of alkenes under a pressure of 2-6 Mpa. and 0-40° C.

In a sixth embodiment of the first aspect of the present invention there is provided a method of producing iodoalkanes by hydroiodination of alkenes wherein the alkene, transition metal precursor and phosphine ligand are dissolved in a solvent.

In a seventh embodiment of the first aspect of the present invention there is provided a method of producing iodoalkanes by hydroiodination of alkenes wherein the solvent is toluene, dichloroethane (DCE) or dichloromethane (DCM).

In an eighth embodiment of the first aspect of the present invention there is provided a method of producing iodoalkanes by hydroiodination of alkenes comprising the reaction of

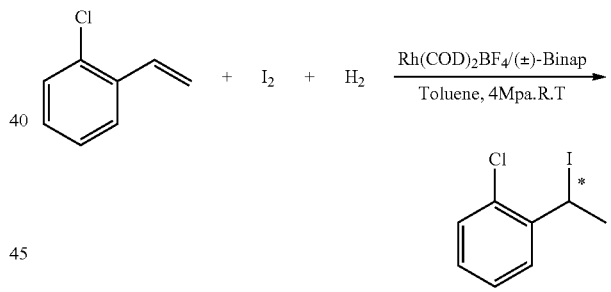

In a ninth embodiment of the first aspect of the present invention there is provided a method of producing iodoalkanes by hydroiodination of alkenes comprising the reaction of

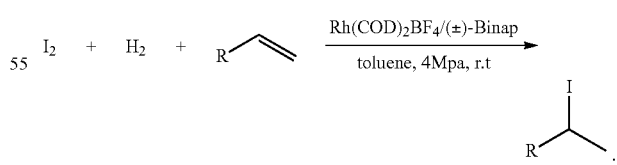

In a tenth embodiment of the first aspect of the present invention there is provided a method of producing iodoalkanes by hydroiodination of alkenes comprising the steps mixing the transition metal precursor, the phosphine ligand, a solvent to produce a first solution;

stirring the first solution at room temperature to produce a second solution;

adding iodine and alkene to the second solution to produce a reaction mixture;
autoclaving the reaction mixture;
stirring the reaction mixture at room temperature under a pressure of 4 Mpa;
removing the solvent to produce a residue; and
purifying the residue to produce the iodoalkane.

In a eleventh embodiment of the first aspect of the present invention there is provided a method of producing iodoalkanes by hydroiodination of alkenes wherein the ratio of alkene to iodine to transition metal precursor to phosphine ligand is 1:1:0.05:0.065.

In a twelfth embodiment of the first aspect of the present invention there is provided a method of producing iodoalkanes by hydroiodination of alkenes wherein the transition metal precursor 0.01%-5% of the reaction mixture and the phosphine ligand is 0.01%-6% of the reaction mixture.

In a thirteenth embodiment of the first aspect of the present invention there is provided a method of producing iodoalkanes by hydroiodination of alkenes wherein the reaction mixture is stirred for 6 to 96 hours.

In a fourteenth embodiment of the first aspect of the present invention there is provided a method of producing iodoalkanes by hydroiodination of alkene wherein method is performed under a pressure of 4 Mpa and at 20-25° C.

In a second aspect of the present invention there is provided an apparatus for producing iodoalkanes using the method of producing iodoalkanes by hydroiodination of alkenes under atmospheric pressure, in room temperature and with the use of metal precursor and ligand as catalyst.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Other aspects and advantages of the invention will be apparent to those skilled in the art from a review of the ensuing description.

DETAILED DESCRIPTION

The present invention is not to be limited in scope by any of the specific embodiments described herein. The following embodiments are presented for exemplification only.

Without wishing to be bound by theory, the inventors have discovered through their trials, experimentations and research that to accomplish the task of an atom economic procedure of preparing iodoalkanes by hydroiodination of alkenes.

The hydrogenation reaction of alkenes, represents an example of hydrogen activation by transition metal catalyst and is the most wildly used reaction in organic chemistry industry. The reaction mechanism for hydrogenation reactions was known as Horiuti-Polanyi mechanism, which describes hydrogen molecule dissociation followed by the sequential addition of atomic hydrogen to the alkenes. The inventors show in the present application using iodine as an atomic hydrogen acceptor result in generation of anhydrous hydrogen iodide. Herein, the inventors describe a new preparation method for iodoalkanes via the hydroiodination reactions of alkenes by anhydrous hydrogen iodide generated in situ from molecular hydrogen catalyzed by a transition metal precursor-ligand catalyst. The present invention provides a method of producing iodoalkane with a product yield of at least 70%. In some embodiment, the present method results in at least 80% yield of iodoalkane. In some embodiment, the product yield of iodoalkane by the method of the present invention is over 90%.

Initial trials are carried out with a complex of $Rh(COD)BF_4$ and $PPh_3$ as catalyst, DCE as solvent, and performed under a hydrogen atmosphere of 4 MPa. The inventors have observed the fading of puce iodine solution, and finally a light yellow solution is obtained and give the addition product 1-iodo-1-phenylethane in 75% yield in 4 hours (Table 1, entry 1). Referring to Table 1, to improve the reaction yield, alternative phosphine ligands are screened. The ratio of alkene to iodine to metal precursor to ligand of the present method is 1:1:0.05:0.065. Reaction conditions of Table 1: styrene (0.2 mmol), styrene/$I_2$/Metal/Ligand (1:1:0.05:0.065), in DME (2 mL) at room temperature under $H_2$ with a pressure of 4 Mpa for 48 hours. The results show phosphine ligand promotes hydroiodination reaction. Phosphine ligands suitable for use in the method of the present invention includes, but are not limited to, (±)-2,2'-Bis(diphenylphosphino)-1,1'-binaphthyl ((±)-Binap), triphenylphosphine ($PPH_3$), ethylenebis(diphenylphosphine) (DPPE), 1,4-bis(diphenylphosphino)butane (DPPB), 4,5-Bis(diphenylphosphino)-9,9-dimethylxanthene (XANTPHOS) and tricyclohexyphosphine, In an embodiment, the phosphine ligand of the present invention is (±)-Binap. Using (±)-Binap as the ligand, various transition metal precursors including rhodium, palladium, iridium, and ruthenium precursors are next tested. The transition metal precursor of the present invention includes, but are not limited to, $Rh(COD)_2BF_4$, $Rh(CO)_2(C_5H_7O_2)$, $[Rh(COD)Cl]_2$, $Rh(COD)_2SbF_6$, $Rh(COD)_2OTf$, $C_{14}H_{16}Cl_2Rh_2$, $[Ir(COD)Cl]_2$, and $Ru(COD)Cl_2$. The results indicate that most of tested transition metal catalysts promote hydroiodination reaction, and $Rh(COD)_2BF_4$ is the preferred embodiment (entry 2, 84% yield). However, $RhCl_3 \cdot 3H_2O$, $[Rh(C_5Me_5)Cl_2]_2$ and palladium catalysts show little activities (entry 10-11, 15-16). The hydroiodination reaction is shown below:

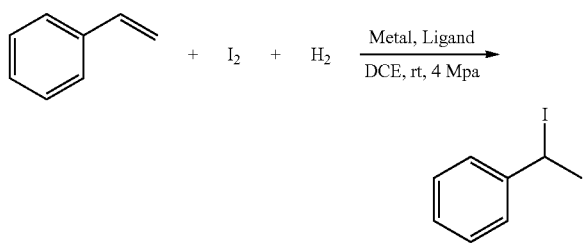

TABLE 1

Product yield of iodoalkane from different combination of ligands and transition-metal precursors. Reaction conditions: styrene (0.2 mmol), styrene/$I_2$/Metal/Ligand (1:1:0.05:0.065), in DME (2 mL) at room temperature under $H_2$ with a pressure of 4 Mpa for 48 hours.

| Entry | Metal precursor | Ligand | Yield/%[a] |
|---|---|---|---|
| 1 | $Rh(COD)_2BF_4$ | $PPh_3$ | 75 |
| 2 | $Rh(COD)_2BF_4$ | (±)-Binap | 84 |
| 3 | $Rh(COD)_2BF_4$ | dppe | 80 |
| 4 | $Rh(COD)_2BF_4$ | dppb | 72 |
| 5 | $Rh(COD)_2BF_4$ | dppf | 79 |
| 6 | $Rh(COD)_2BF_4$ | XANTPHOS | 70 |
| 7 | $Rh(COD)_2BF_4$ | Tricyclohexylphosphine | 77 |
| 8 | $Rh(CO)_2(C_5H_7O_2)$ | (±)-Binap | 61 |

TABLE 1-continued

Product yield of iodoalkane from different combination of ligands and transition-metal precursors. Reaction conditions: styrene (0.2 mmol), styrene/I$_2$/Metal/Ligand (1:1:0.05:0.065), in DME (2 mL) at room temperature under H$_2$ with a pressure of 4 Mpa for 48 hours.

| Entry | Metal precursor | Ligand | Yield/%[a] |
|---|---|---|---|
| 9 | [Rh(COD)Cl]$_2$ | (±)-Binap | 53 |
| 10 | RhCl$_3$·3H$_2$O | (±)-Binap | trace |
| 11 | [Rh(C$_5$Me$_5$)Cl$_2$]$_2$ | (±)-Binap | N.R |
| 12 | Rh(COD)$_2$SbF$_6$ | (±)-Binap | 72 |
| 13 | Rh(COD)$_2$OTf | (±)-Binap | 47 |
| 14 | C$_{14}$H$_{16}$Cl$_2$Rh$_2$ | (±)-Binap | 51 |
| 15 | Pd(OAC)$_2$ | (±)-Binap | trace |
| 16 | [PdCl(C$_3$H$_5$)]$_2$ | (±)-Binap | N.R |
| 17 | [Ir(COD)Cl]$_2$ | (±)-Binap | 58 |
| 18 | Ru(COD)Cl$_2$ | (±)-Binap | 56 |

[a]Isolated Yield.
Note:
COD = 1,5-cyclooctadiene; [PdCl(C$_3$H$_5$)]$_2$ = allylpalladium(II) chloride dimer; [Rh(C$_5$Me$_5$)Cl$_2$]$_2$ = pentamethylcyclo-pentadienylrhodium(III) chloride dimer.
Ligands

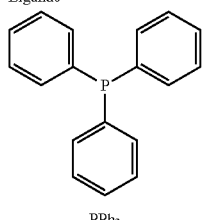

PPh$_3$

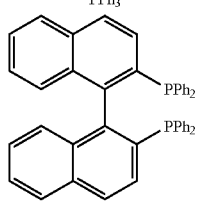

rac-Binap

DPPE

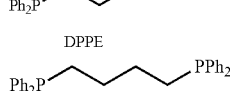

DPPB

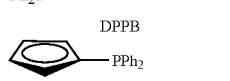

DPPF

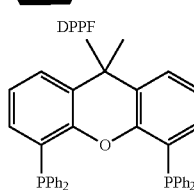

Xantphos

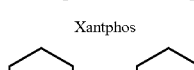

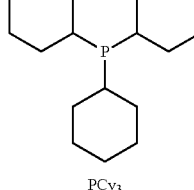

PCy$_3$

The reaction solvent, temperature, and pressure are next investigated. The results are compiled in Table 2. The solvent test results show solvents of the hydroiodination reaction of the present invention are DCE, toluene, and DCM (entry 1-3). Other solvents, including DMA, DMF, MTBE, i-PrOH, and DME are not suitable solvent (entry 4-8). Hydroiodination of the present method is performed in 0-40° C. and under pressure ranges from 2-6 MPa. In another embodiment, the present method is performed at 20-25° C. The inventors of the present application has found that hydroiodination outside the temperatures and pressures of the present method reduce the product yield to lower than 80%. The following temperature and pressure experiments indicate that the best reaction result is obtained at room temperature and under a pressure of 4 MPa. Increasing the reaction temperature or pressure of hydrogen proved detrimental to this result (entry 9-13).

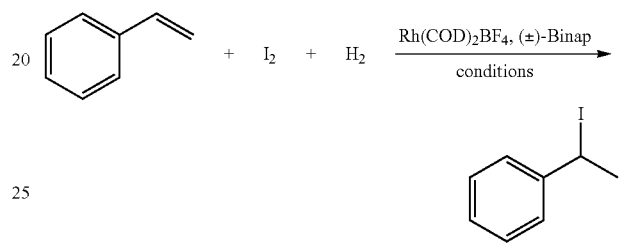

TABLE 2

Product yield of iodoalkane under different temperatures and pressures. Reaction conditions: styrene (0.2 mmol), styrene/I$_2$/Rh(COD)$_2$BF$_4$/(±)-Binap (1:1:0.05:0.065), in DME (2 mL) at room temperature under H$_2$ with a pressure of 4 Mpa for 48 hours.

| Entry | Solvent | Temperature(° C.) | Pressure(MPa) | Yield(%)[a] |
|---|---|---|---|---|
| 1 | DCE | r.t. | 4 | 84 |
| 2 | Toluene | r.t. | 4 | 88 |
| 3 | DCM | r.t. | 4 | 50 |
| 4 | DMA | r.t. | 4 | N.R |
| 5 | DMF | r.t. | 4 | N.R |
| 6 | MTBE | r.t. | 4 | N.R |
| 7 | i-PrOH | r.t. | 4 | N.R |
| 8 | DME | r.t. | 4 | trace |
| 9 | Toluene | 0 | 4 | 82 |
| 10 | Toluene | 40 | 4 | 75 |
| 11 | Toluene | r.t. | 2 | 68 |
| 12 | Toluene | r.t. | 3 | 73 |
| 13 | Toluene | r.t. | 6 | 83 |

[a]Isolated Yield.

With the optimized reaction conditions in hand (5 mol % of Rh(COD)$_2$BF$_4$, 6 mol % of Binap, toluene as solvent and perform under 4 MPa at room temperature), the scope and limitations for this hydroiodination reaction of various alkenes is investigated. The results are compiled in Table 3. Table 3 shows the product yield of one embodiment of the present method, styrene (0.2 mmol) is hydroiodinated in the following ratios: 1:1:0.05:0.065 of styrene/I$_2$/Rh(COD)$_2$BF$_4$/(±)-Binap, in DME (2 mL) at room temperature under H$_2$ with a pressure of 4 Mpa for indicated period of time. Most of the alkenes, inhydroiodination reaction, proceed smoothly to afford corresponding iodoalkanes as Markovnikov addition products. Notably, high reaction yields are achieved by halogenated styrene (entry 2-9), diphenylethene (entry 15, 16) and linear terminal alkenes (entry 19-21). However, trimethyl-2-vinylbenzene gives no product probably due to steric hindrance (entry 12). Electron donating group substituted alkenes such as 1-methyl-4-vinylbenzene, 1-methoxy-4-vinylbenzene, vinylcyclohexane and oct-1-ene are less active in hydroiodination, especially for para-methoxyl-styrene (entry 10, 13, 17 and 23). 1,2-Dihydronaphthalene and 1,4-dihydronaphthalene are also not suitable for present reaction (entry 24 and 25).

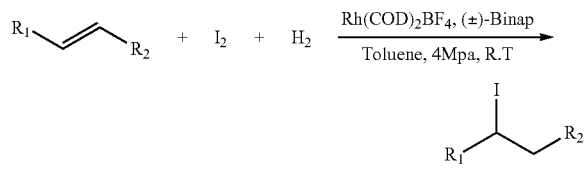

TABLE 3

Product yield of iodoalkane prepared from different alkenes. Reaction conditions: styrene (0.2 mmol), styrene/I$_2$/Rh(COD)$_2$BF$_4$/(±)-Binap (1:1:0.05:0.065), in DME (2 mL) at room temperature under H$_2$ with a pressure of 4Mpa for indicated period of time.

| Entry | Alkenes | Time (h) | Yield(%)[a] |
|---|---|---|---|
| 1 | styrene | 24 | 88 |
| 2 | 4-F-styrene | 24 | 92 |
| 3 | 3-F-styrene | 24 | 90 |
| 4 | 2-F-styrene | 12 | 99 |
| 5 | 4-Cl-styrene | 6 | 99 |
| 6 | 3-Cl-styrene | 6 | 99 |
| 7 | 2-Cl-styrene | 6 | 99 |
| 8 | 4-Br-styrene | 6 | 99 |
| 9 | 3-Br-styrene | 6 | 98 |
| 10 | 4-Me-styrene | 48 | 52 |
| 11 | 2,4-diMe-styrene | 96 | 83 |
| 12 | 2,4,6-triMe-styrene | 96 | TRACE |
| 13 | 4-OMe-styrene | 96 | NR |
| 14 | 4-phenyl-styrene | 24 | 81 |
| 15 | cis-stilbene | 12 | 99 |
| 16 | trans-stilbene | 72 | 99 |
| 17 | vinylcyclohexane | 72 | 66 |
| 18 | hex-1-ene | 24 | 76 |
| 19 | dodec-1-ene | 6 | 99 |
| 20 | allylbenzene | 24 | 96 |
| 21 | but-3-enylbenzene | 24 | 99 |

TABLE 3-continued

Product yield of iodoalkane prepared from different alkenes. Reaction conditions: styrene (0.2 mmol), styrene/I$_2$/Rh(COD)$_2$BF$_4$/(±)-Binap (1:1:0.05:0.065), in DME (2 mL) at room temperature under H$_2$ with a pressure of 4Mpa for indicated period of time.

| Entry | Alkenes | Time (h) | Yield(%)[a] |
|---|---|---|---|
| 22 | 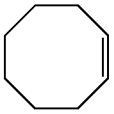 | 72 | 91 |
| 23 |  | 72 | 55 |
| 24 | 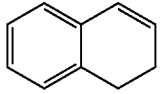 | 96 | Trace |
| 25 | 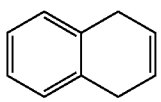 | 96 | Trace |

[a]Isolated Yield.

The present invention provides a high atom economic method of hydroiodination for the preparation of iodoalkanes from alkenes. As the amount of catalyst is an essential element in chemistry industry, the inventors next explore the utility of present reaction with different catalyst loadings (Table 4). When the catalyst loading decreases to 0.1% Rh(COD)$_2$BF$_4$ and 0.12% (±)-Binap, the hydroiodination remains proceed in a high yield. (entry 3, 94% yield) Further decreasing of catalyst loading decreases the reaction yield dramatically (entry 4-6). Apparently, no reaction takes place in the absence of catalyst (entry 7). Therefore, the present hydroiodination can be realized in high yield (>90%) by an extremely low catalyst loading of 0.1% or down to 0.01% accordingly to the present method. In one embodiment, at least 0.01% of metal precursor and 0.012% of ligand are used in the present method to result over 80% product yield.

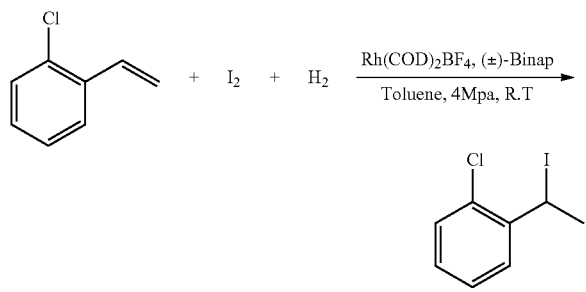

TABLE 4

Catalyst loading of hydroiodination reaction. Reaction conditions: 1-chloro-2-vinylbenzene (0.2 mmol), 1-chloro-2-vinylbenzene/I$_2$/Rh(COD)$_2$BF$_4$/(±)-Binap (1:1:0.05:0.065), in DME (2 mL) at room temperature under H$_2$ with a pressure of 4 Mpa.

| Entry | Metal | Ligand | Yield/%[a] |
|---|---|---|---|
| 1 | 5% | 6% | 99 |
| 2 | 1% | 1.2% | 96 |
| 3 | 0.1% | 0.12% | 94 |
| 4 | 0.01% | 0.012% | 86 |
| 5 | 0.001% | 0.0012% | 62 |
| 6 | 0.0001% | 0.00012% | Trace |
| 7 | 0% | 0% | N.R |

[a]Isolated Yield.

In conclusion, the present application provides the first catalytic preparing method of iodoalkane from anhydrous hydrogen iodide using iodine and hydrogen. The method of the present application synthesizing iodoalkanes from hydroiodination of aryl and alkyl alkenes results in >80% high yield. Notably, the present method has provided an atom economic procedure for preparing anhydrous hydrogen iodide, which offers a promising future for its further utilization in other hydrogen iodide participating reactions. One embodiment of rhodium catalyzed hydroiodination reactions of alkenes of the present invention:

Rh(COD)$_2$BF$_4$ (4.1 mg, 0.01 mmol), (±)-Binap (8.1 mg, 0.013 mmol), and 1.0 mL toluene are added to a tube under argon atmosphere. The resulting solution is stirred at room temperature for 30 min. Then iodine (50.8 mg, 0.2 mmol) and alkene (0.2 mmol) dissolved in toluene (2 ml) are added, and the tube is subjected to a mini autoclave. After the hydrogen replacement, the reaction mixture is stirred at room temperature for 48 hours under a pressure of 4 Mpa. Then toluene solvent is removed by vacuum evaporation, and the residue is purified by silica gel column chromatography to obtain the iodoalkane as desired product.

INDUSTRIAL APPLICATION

The present invention relates to an atom economic procedure of preparing iodoalkanes by hydroiodination of alkenes. In particular the present method features the generation of anhydrous hydrogen iodide from atomic hydrogen and iodine in situ by using transition metal precursor and phosphine ligandas catalyst.

The invention claimed is:

1. A method of producing iodoalkanes comprising hydroiodinating alkene with hydrogen and iodine with a transition metal precursor and a phosphine ligand as catalyst, wherein said metal precursor is selected from the group consisting of a Rh(COD)$_2$BF$_4$, Rh(CO)$_2$(C$_5$H$_7$O$_2$), [Rh(COD)Cl]$_2$, Rh(COD)$_2$SbF$_6$, Rh(COD)$_2$OTf, C$_{14}$H$_{16}$Cl$_2$Rh$_2$, [Ir(COD)Cl]$_2$, and Ru(COD)Cl$_2$.

2. The method according to claim 1, further comprising converting the hydrogen and iodine into anhydrous hydrogen iodide.

3. The method according to claim 1 wherein said hydroiodinating step is performed in situ and the hydrogen and iodine are atomic hydrogen and iodine.

4. The method according to claim 1 wherein the phosphine ligand is selected from the group consisting of (±)-2,2'-Bis(diphenylphosphino)-1,1'-binaphthyl ((±)-Binap), triphenylphosphine (PPH$_3$), ethylenebis(diphenylphosphine) (DPPE), 1,4-bis(diphenylphosphino)butane (DPPB), 4,5-Bis(diphenylphosphino)-9,9-dimethylxanthene (XANTPHOS), 1,1'-Ferrocenediyl-bis(diphenylphosphine) (DPPF), and tricyclohexyphosphine.

5. The method according to claim 1 wherein the method is performed under a pressure of 2-6 Mpa and at 0-40° C.

6. The method according to claim 1 wherein the alkene, transition metal precursor and phosphine ligand are dissolved in a solvent.

7. The method according to claim 6 wherein the solvent is selected from the group consisting of dichloroethane (DCE), toluene, and dichloromethane (DCM).

8. The method according to claim 1, wherein the hydroiodinating step is

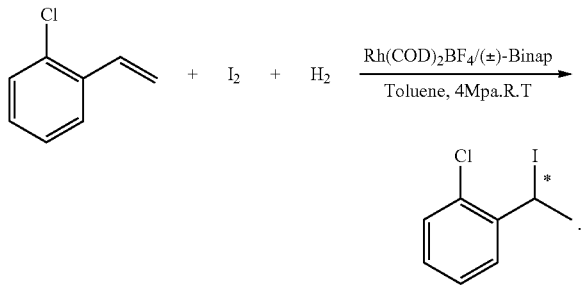

9. The method according to claim 1, wherein the hydroiodinating step is

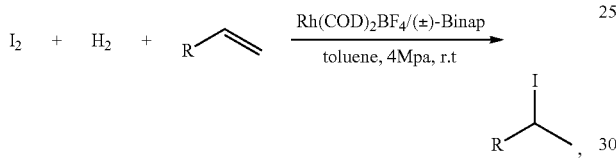

wherein R is phenyl, 4-fluorophenyl, 3-fluorophenyl, 2-fluorophenyl, 4-chlorophenyl, 3-chlorophenyl, 2-chlorophenyl, 4-bromophenyl, 3-bromophenyl, 4-methylphenyl, 2,5-dimethylphenyl, 2,4,6-trimethylphenyl, 4-methoxyphenyl, 4-phenylbenzene, cyclohexyl, n-hexyl, n-dodecyl, benzyl, or phenethyl.

10. The method according to claim 1, wherein the hydroiodinating step comprises
mixing the transition metal precursor, the phosphine ligand, a solvent to produce a first solution;
stirring the first solution at room temperature to produce a second solution;
adding iodine and alkene to the second solution to produce a reaction mixture;
autoclaving the reaction mixture;
stirring the reaction mixture at room temperature under a pressure of 4 Mpa;
removing the solvent to produce a residue; and
purifying the residue to obtain the iodoalkane.

11. The method according to claim 1, wherein the ratio of alkene to iodine to transition metal precursor to phosphine ligand is 1:1:0.05:0.065.

12. The method according to claim 1, wherein the transition metal precursor is 0.01%-5% of the reaction mixture and the phosphine ligand is 0.01%-6% of the reaction mixture.

13. The method according to claim 11, wherein the reaction mixture is stirred for 6 to 96 hours.

14. The method according to claim 5, wherein method is performed under a pressure of 4 Mpa and at 20-25° C.

* * * * *